US012746058B2

(12) United States Patent
Koop et al.

(10) Patent No.: US 12,746,058 B2
(45) Date of Patent: Sep. 29, 2026

(54) POINT PULSED FIELD ABLATION CATHETER

(71) Applicant: Boston Scientific Scimed Inc., Maple Grove, MN (US)

(72) Inventors: Brendan E. Koop, Ham Lake, MN (US); Andrew L. De Kock, Ham Lake, MN (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 1043 days.

(21) Appl. No.: 17/825,456

(22) Filed: May 26, 2022

(65) Prior Publication Data

US 2022/0378502 A1 Dec. 1, 2022

Related U.S. Application Data

(60) Provisional application No. 63/194,716, filed on May 28, 2021.

(51) Int. Cl.
*A61B 18/00* (2006.01)
*A61B 18/14* (2006.01)

(52) U.S. Cl.
CPC *A61B 18/1492* (2013.01); *A61B 2018/00577* (2013.01); *A61B 2018/00613* (2013.01); *A61B 2018/00702* (2013.01); *A61B 2018/00875* (2013.01); *A61B 2018/1407* (2013.01)

(58) Field of Classification Search
None
See application file for complete search history.

(56) References Cited

U.S. PATENT DOCUMENTS

2010/0130854 A1* 5/2010 Shachar .................. A61B 5/06 600/424
2013/0006238 A1* 1/2013 Ditter ................ A61B 18/1492 606/41

(Continued)

FOREIGN PATENT DOCUMENTS

WO 2015/103530 A1 7/2015
WO 2015/103574 A1 7/2015

(Continued)

OTHER PUBLICATIONS

Annotated Ditter Fig 15A (Year: 2025).*

(Continued)

*Primary Examiner* — Linda C Dvorak
*Assistant Examiner* — Nicholas S Borsch
(74) *Attorney, Agent, or Firm* — Nelson Mullins Riley & Scarborough LLP

(57) ABSTRACT

Various aspects of the present disclosure are directed towards apparatuses, systems and methods that may include an electroporation ablation device. The electroporation ablation device may include a shaft defining a longitudinal axis and an electrode assembly including a first pair of electrodes having a first electrode and a second electrode, and a second pair of electrodes disposed adjacent to the first pair of electrodes and having a third and a fourth electrode. In some embodiments, the first electrode has a first edge portion, and a first side view of the first edge portion along the longitudinal axis is rounded at a first corner.

20 Claims, 7 Drawing Sheets

(56) References Cited

U.S. PATENT DOCUMENTS

| | | | | |
|---|---|---|---|---|
| 2016/0166310 | A1* | 6/2016 | Stewart | A61B 18/1492 606/34 |
| 2019/0150842 | A1 | 5/2019 | Shuros et al. | |
| 2020/0397505 | A1 | 12/2020 | Viswanathan et al. | |

FOREIGN PATENT DOCUMENTS

| | | | |
|---|---|---|---|
| WO | 2018/201037 | A1 | 11/2018 |
| WO | 2019/143960 | A1 | 7/2019 |
| WO | 2019/234133 | A1 | 12/2019 |
| WO | 2020/206328 | A1 | 10/2020 |
| WO | 2021009648 | A1 | 2/2021 |

OTHER PUBLICATIONS

Annotated Ditter Fig 15B (Year: 2025).*

International Preliminary Report on Patentability and Written Opinion for PCT Application No. PCT/US2022/031063 mailed Dec. 7, 2023. 8 pages.

Brochure., "Sicherheit im Mittelpunkt", Medline International Germany GmbH, Oct. 2016.

Kennedy et al., "Quantification of Electroporative Uptake Kinetics and Electric Field Heterogeneity Effects in Cells" Biophys J, vol. 94, No. 12, Mar. 13, 2008, pp. 5018-5027.

Raso et al., "Recommendations guidelines on the key information to be reported in studies of application of PEF technology in food and biotechnological processes", Innovative Food Science & Emerging Technologies, vol. 37, Oct. 2016, pp. 312-321.

* cited by examiner

POINT PULSED FIELD ABLATION CATHETER

CROSS REFERENCE TO RELATED APPLICATION

This application claims priority to Provisional Application No. 63/194,716, filed May 28, 2021, which is herein incorporated by reference in its entirety.

TECHNICAL FIELD

The present disclosure relates to medical apparatus, systems, and methods for cardiac electroporation ablation. More specifically, the present disclosure relates to a point pulsed field ablation catheter.

BACKGROUND

Ablation procedures are used to treat many different conditions in patients. Ablation may be used to treat cardiac arrhythmias, benign tumors, cancerous tumors, and to control bleeding during surgery. Usually, ablation is accomplished through thermal ablation techniques including radio-frequency (RF) ablation and cryoablation. In RF ablation, a probe is inserted into the patient and radio frequency waves are transmitted through the probe to the surrounding tissue. The radio frequency waves generate heat, which destroys surrounding tissue and cauterizes blood vessels. In cryoablation, a hollow needle or cryoprobe is inserted into the patient and cold, thermally conductive fluid is circulated through the probe to freeze and kill the surrounding tissue. RF ablation and cryoablation techniques indiscriminately kill tissue through cell necrosis, which may damage or kill otherwise healthy tissue, such as tissue in the esophagus, phrenic nerve cells, and tissue in the coronary arteries.

Another ablation technique uses electroporation. In electroporation, or electro-permeabilization, an electric field is applied to cells to increase the permeability of the cell membrane. The electroporation may be reversible or irreversible, depending on the strength of the electric field. If the electroporation is reversible, the increased permeability of the cell membrane may be used to introduce chemicals, drugs, and/or deoxyribonucleic acid (DNA) into the cell, prior to the cell healing and recovering. If the electroporation is irreversible, the affected cells are killed through apoptosis.

Irreversible electroporation (IRE) may be used as a non-thermal ablation technique. In IRE, trains of short, high voltage pulses are used to generate electric fields that are strong enough to kill cells through apoptosis. In ablation of cardiac tissue, IRE may be a safe and effective alternative to the indiscriminate killing of thermal ablation techniques, such as RF ablation and cryoablation. IRE may be used to kill target tissue, such as myocardium tissue, by using an electric field strength and duration that kills the target tissue but does not permanently damage other cells or tissue, such as non-targeted myocardium tissue, red blood cells, vascular smooth muscle tissue, endothelium tissue, and nerve cells.

During IRE procedures, sometimes at higher output energy from the ablation catheter, adverse events may happen such as the formation of arc or spark. The formation of arc or spark can cause tissue damage and increase risk for treatment of the patient. A way to prevent or reduce the formation of arc or spark during IRE procedures is needed.

SUMMARY

In Example 1, an electroporation ablation device comprises a shaft having an elongated body defining a longitudinal axis, the elongated body having a distal end and a proximal end and an electrode assembly disposed on the shaft. The electrode assembly comprises a first pair of electrodes comprising a first electrode disposed proximate to the distal end of the elongated body and a second electrode and a second pair of electrodes disposed adjacent to the first pair of electrodes and comprising a third electrode and a fourth electrode. The first electrode comprises a first edge portion generally perpendicular to the longitudinal axis. The second electrode comprises a second edge portion generally perpendicular to the longitudinal axis and a third edge portion generally perpendicular to the longitudinal axis. The first edge portion is closer to the second edge portion than the third edge portion. A first side view of the first edge portion along the longitudinal axis is rounded at a first corner with a first edge radius, and a second side view of the second edge portion is rounded at a second corner with a second edge radius.

In Example 2, the electroporation ablation device of Example 1, wherein the first electrode has a first electrode surface area, the second electrode has a second electrode surface area, and a difference between the first electrode surface area and the second electrode surface area is less than 20% of the first electrode surface area.

In Example 3, the electroporation ablation device of Example 2, wherein the difference between the first electrode surface area and the second electrode surface area is less than 10% of the first electrode surface area.

In Example 4, the electroporation ablation device of any of Examples 1-3, wherein a distance between the first edge portion and the second edge portion is in the range of 1 millimeter and 2 millimeters.

In Example 5, the electroporation ablation device of any of Examples 1-3, wherein a distance between the first edge portion and the second edge portion is in the range of 1.4 millimeter and 1.8 millimeter.

In Example 6, the electroporation ablation device of any of Examples 1-5, wherein the second pair of electrodes are sensing electrodes configured to measure an electrical signal, and are disposed between the first electrode and the second electrode.

In Example 7, the electroporation ablation device of any of Examples 1-6, wherein the electrode assembly further comprises a fifth ring electrode disposed further away from the distal end of the elongated body than each electrode of the first pair of electrodes.

In Example 8, the electroporation ablation device of any of Examples 1-7, wherein the first electrode comprises a conductive material having a first thickness, wherein the first edge radius is associated with the first thickness, and wherein the second electrode comprises a conductive material having a second thickness, wherein the second edge radius is associated with the second thickness.

In Example 9, a method for electroporation ablations comprises disposing a point electroporation catheter proximate to target tissue, the point electroporation catheter comprising a shaft defining a longitudinal axis and a first pair of electrodes, the first pair of electrodes comprising a first electrode disposed proximate to a distal end of the shaft and a second electrode disposed proximate to the first electrode, the first electrode having a first electrode surface area, the second electrode having a second electrode surface area, a difference between the first electrode surface area and the second electrode surface area being less than 20% of the first electrode area, and generating an electric field, by the first pair of electrodes, in the target tissue in response to a plurality of electrical pulse sequences delivered in a plurality of therapy sections, the electric field having electric field strength sufficient to ablate the target tissue via irreversible electroporation.

In Example 10, the method of Example 9, wherein the point electroporation catheter further comprises a second pair of electrodes disposed adjacent to the first pair of electrodes and comprising a third electrode and a fourth electrode.

In Example 11, the method of any of Examples 9-10, further comprising collecting sensing signals by the second pair of electrodes, and determining a location of the point electroporation catheter based on the collected sensing signals.

In Example 12, the method of any of Examples 9-11, wherein the first electrode comprises a first edge portion generally perpendicular to the longitudinal axis, the second electrode comprises a second edge portion generally perpendicular to the longitudinal axis and a third edge portion generally perpendicular to the longitudinal axis, and the first edge portion is closer to the second edge portion than the third edge portion.

In Example 13, the method of any of Examples 9-12, wherein a first cross-sectional shape of the first edge portion along the longitudinal axis is rounded at a first corner with a first edge radius.

In Example 14, the method of any of Examples 9-13, wherein a second cross-sectional shape of the second edge portion along the longitudinal axis is rounded at a second corner with a second edge radius.

In Example 15, the method of any of Examples 9-14, further comprising: collecting sensing signals by the second pair of electrodes; and determining a location of the point electroporation catheter based on the collected sensing signals.

In Example 16, an electroporation ablation device comprises a shaft having an elongated body defining a longitudinal axis, the elongated body having a distal end and a proximal end, and an electrode assembly disposed on the shaft. The electrode assembly comprises a first pair of electrodes comprising a first electrode disposed proximate to the distal end of the elongated body and a second electrode and a second pair of electrodes disposed adjacent to the first pair of electrodes and comprising a third electrode and a fourth electrode. The first electrode comprises a first edge portion generally perpendicular to the longitudinal axis. The second electrode comprises a second edge portion generally perpendicular to the longitudinal axis and a third edge portion generally perpendicular to the longitudinal axis. The first edge portion is closer to the second edge portion than the third edge portion. A first side view of the first edge portion along the longitudinal axis is rounded at a first corner with a first edge radius, and a second side view of the second edge portion is rounded at a second corner with a second edge radius.

In Example 17, the electroporation ablation device of Example 16, wherein the first electrode has a first electrode surface area, the second electrode has a second electrode surface area, and a difference between the first electrode surface area and the second electrode surface area is less than 20% of the first electrode surface area.

In Example 18, the electroporation ablation device of Example 16, wherein the difference between the first electrode surface area and the second electrode surface area is less than 10% of the first electrode surface area.

In Example 19, the electroporation ablation device of Example 16, wherein a distance between the first edge portion and the second edge portion is in the range of 1 millimeter and 2 millimeters.

In Example 20, the electroporation ablation device of Example 16, wherein a distance between the first edge portion and the second edge portion is in the range of 1.4 millimeter and 1.8 millimeter.

In Example 21, the electroporation ablation device of Example 16, wherein the second pair of electrodes are sensing electrodes configured to measure an electrical signal.

In Example 22, the electroporation ablation device of Example 20, wherein the second pair of electrodes are disposed between the first electrode and the second electrode.

In Example 23, the electroporation ablation device of Example 16, wherein the electrode assembly further comprises a fifth ring electrode disposed further away from the distal end of the elongated body than each electrode of the first pair of electrodes.

In Example 24, the electroporation ablation device of Example 16, wherein the first electrode comprises a conductive material having a first thickness, wherein the first edge radius is associated with the first thickness.

In Example 25, the electroporation ablation device of Example 16, wherein the second electrode comprises a conductive material having a second thickness, wherein the second edge radius is associated with the second thickness.

In Example 26, a method for electroporation ablations comprises disposing a point electroporation catheter proximate to target tissue, the point electroporation catheter comprising a shaft defining a longitudinal axis and a first pair of electrodes, the first pair of electrodes comprising a first electrode disposed proximate to a distal end of the shaft and a second electrode disposed proximate to the first electrode, the first electrode having a first electrode surface area, the second electrode having a second electrode surface area, a difference between the first electrode surface area and the second electrode surface area being less than 20% of the first electrode area, and generating an electric field, by the first pair of electrodes, in the target tissue in response to a plurality of electrical pulse sequences delivered in a plurality of therapy sections, the electric field having electric field strength sufficient to ablate the target tissue via irreversible electroporation.

In Example 27, the method of Example 26, wherein the point electroporation catheter further comprises a second pair of electrodes disposed adjacent to the first pair of electrodes and comprising a third electrode and a fourth electrode.

In Example 28, the method of Example 27, further comprising collecting sensing signals by the second pair of electrodes.

In Example 29, the method of Example 28, further comprising determining a location of the point electroporation catheter based on the collected sensing signals.

In Example 30, the method of Example 26, wherein the first electrode comprises a first edge portion generally perpendicular to the longitudinal axis.

In Example 31, the method of Example 30, wherein the second electrode comprises a second edge portion generally perpendicular to the longitudinal axis and a third edge portion generally perpendicular to the longitudinal axis.

In Example 32, the method of Example 31, wherein the first edge portion is closer to the second edge portion than the third edge portion.

In Example 33, the method of Example 32, wherein a first cross-sectional shape of the first edge portion along the longitudinal axis is rounded at a first corner with a first edge radius.

In Example 34, the method of Example 33, wherein a second cross-sectional shape of the second edge portion is rounded at a second corner with a second edge radius.

In Example 35, an electroporation ablation system for treating target tissue in a patient comprises an electroporation ablation device. The electroporation ablation device comprises a shaft having an elongated body defining a longitudinal axis, the elongated body having a distal end and a proximal end, and an electrode assembly disposed on the shaft. The electrode assembly comprises a first pair of electrodes comprising a first electrode disposed proximate to the distal end of the elongated body and a second electrode and a second pair of electrodes disposed adjacent to the first pair of electrodes and comprising a third electrode and a fourth electrode. The first electrode comprises a first edge portion generally perpendicular to the longitudinal axis. The second electrode comprises a second edge portion generally perpendicular to the longitudinal axis and a third edge portion generally perpendicular to the longitudinal axis. The first edge portion is closer to the second edge portion than the third edge portion. A first side view of the first edge portion along the longitudinal axis is rounded at a first corner with a first edge radius, and a second side view of the second edge portion is rounded at a second corner with a second edge radius. The electroporation ablation system further comprises a controller configured to receive one or more signals from the one or more mapping electrodes, and an electroporation generator operatively coupled to the electrode assembly and the controller.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
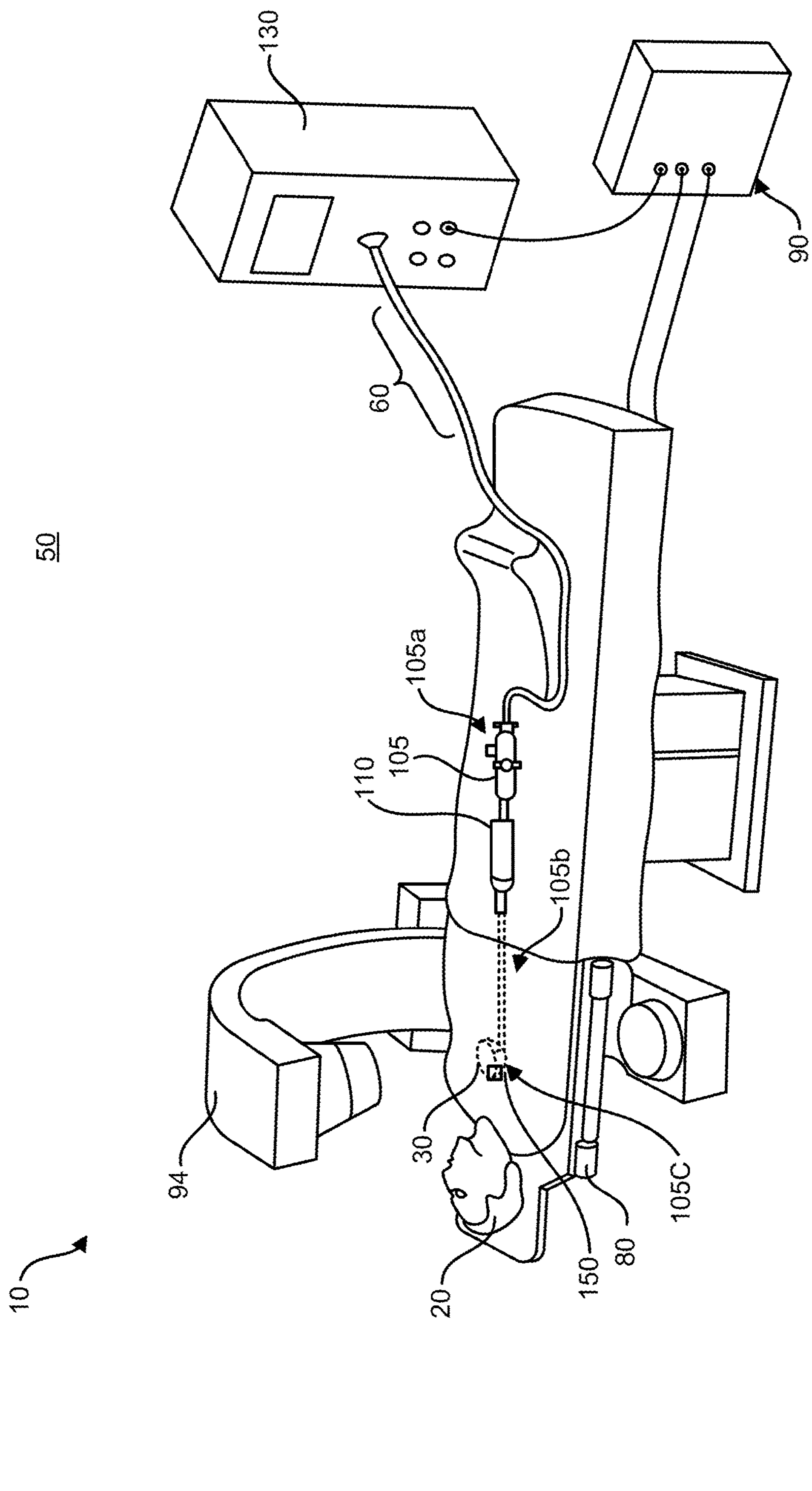
FIG. 1 is a diagram illustrating an exemplary clinical setting for treating a patient and for treating a heart of the patient, using an electrophysiology system, in accordance with embodiments of the subject matter of the disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

The following detailed description is exemplary in nature and is not intended to limit the scope, applicability, or configuration of the invention in any way. Rather, the following description provides some practical illustrations for implementing exemplary embodiments of the present invention. Examples of constructions, materials, and/or dimensions are provided for selected elements. Those skilled in the art will recognize that many of the noted examples have a variety of suitable alternatives.

As the terms are used herein with respect to measurements (e.g., dimensions, characteristics, attributes, components, etc.), and ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), “about” and “approximately” may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

Although illustrative methods may be represented by one or more drawings (e.g., flow diagrams, communication flows, etc.), the drawings should not be interpreted as implying any requirement of, or particular order among or between, various steps disclosed herein. However, certain some embodiments may require certain steps and/or certain orders between certain steps, as may be explicitly described herein and/or as may be understood from the nature of the steps themselves (e.g., the performance of some steps may depend on the outcome of a previous step). Additionally, a “set,” “subset,” or “group” of items (e.g., inputs, algorithms, data values, etc.) may include one or more items, and, similarly, a subset or subgroup of items may include one or more items. A “plurality” means more than one.

As used herein, the term "based on" is not meant to be restrictive, but rather indicates that a determination, identification, prediction, calculation, and/or the like, is performed by using, at least, the term following "based on" as an input. For example, predicting an outcome based on a particular piece of information may additionally, or alternatively, base the same determination on another piece of information.

Irreversible electroporation (IRE) uses high voltage, short (e.g., 100 microseconds or shorter) pulses to kill cells through apoptosis. IRE can be targeted to kill myocardium, sparing other adjacent tissues including the esophageal vascular smooth muscle and endothelium. During the course of IRE therapy sections, adverse events may occur such as the formation of arc or spark. A therapy section may include a therapy bursts period and a quiet period. A therapy section (e.g., for a duration of around 10 milliseconds) may include a plurality of electrical pulses (e.g., 20 pulses, 30 pulses, etc.), also referred to as therapy bursts, generated and delivered continuously by an electroporation generator. The therapy burst period refers to the period of therapy bursts and the quiet period refers to the period without the therapy bursts. In some instances, the arc or spark may occur during the therapy bursts period. The formation of arc or spark can cause tissue damage and increase risk for treatment of the patient.

At least some embodiments of the present disclosure are directed to point electroporation ablation catheter designs to reduce or prevent arc formation during IRE ablation. In some embodiments, an electroporation ablation system includes a point electroporation ablation catheter designed to reduce or prevent arc formation during IRE ablation. As used herein, a point catheter refers to a catheter with a linear body carrying ablation electrodes. In embodiments, a point catheter has ablation electrodes toward its distal end.

FIG. 1 is a diagram illustrating an exemplary clinical setting 10 for treating a patient 20, and for treating a heart 30 of the patient 20, using an electrophysiology system 50, in accordance with embodiments of the subject matter of the disclosure. The electrophysiology system 50 includes an electroporation device 60 and an optional localization field generator 80. Also, the clinical setting 10 includes additional equipment such as imaging equipment 94 (represented by the C-arm) and various controller elements configured to allow an operator to control various aspects of the electrophysiology system 50. As will be appreciated by the skilled artisan, the clinical setting 10 may have other components and arrangements of components that are not shown in FIG. 1.

The electroporation device 60 includes an electroporation catheter 105, an introducer sheath 110, a controller 90, and an electroporation generator 130. In embodiments, the electroporation device 60 is configured to deliver electric field energy to target tissue in the patient's heart 30 to create tissue apoptosis, rendering the tissue incapable of conducting electrical signals. The controller 90 is configured to control functional aspects of the electroporation device 60. In embodiments, the controller 90 is configured to control the electroporation generator 130 to generate electrical pulses, for example, the magnitude of the electrical pulses, the timing and duration of electrics pulses. In embodiments, the electroporation generator 130 is operable as a pulse generator for generating and supplying pulse sequences to the electroporation catheter 105.

In embodiments, the introducer sheath 110 is operable to provide a delivery conduit through which the electroporation catheter 105 may be deployed to the specific target sites within the patient's heart 30. It will be appreciated, however, that the introducer sheath 110 is illustrated and described herein to provide context to the overall electrophysiology system 50.

In the illustrated embodiment, the electroporation catheter 105 includes a handle 105*a*, a shaft 105*b*, and an electrode assembly 150. The handle 105*a* is configured to be operated by a user to position the electrode assembly 150 at the desired anatomical location. The shaft 105*b* has a distal end 105*c* and generally defines a longitudinal axis of the electroporation catheter 105. As shown, the electrode assembly 150 is located at or proximate the distal end 105*c* of the shaft 105*b*. In embodiments, the electrode assembly 150 is electrically coupled to the electroporation generator 130, to receive electrical pulse sequences or pulse trains, thereby selectively generating electrical fields for ablating the target tissue by irreversible electroporation.

In certain embodiments, the electroporation catheter 105 is a point catheter that includes a linear body toward the distal end. In embodiments, the electrode assembly 150 includes one or more electrodes disposed on the shaft 105*b*. In some implementations, the electrode assembly 150 includes one or more electrode pairs. In some embodiments, the electrode assembly 150 includes one or more ablation electrodes and one or more sensing electrodes. In certain implementations, the electrode assembly 150 includes a pair of ablation electrodes configured to generate electrical fields sufficient for irreversible electroporation ablation. In some examples, the ablation electrode pair including a cap electrode covering an end cap of the distal end of the catheter 105 and a ring electrode disposed proximate to the cap electrode. As used herein, a ring electrode refers to an electrode having a ring shape. In some designs, the cap electrode and the ring electrode include edge radius (e.g., rounded edges) at one or more edges, for example, to reduce arcing. In some designs, the pair of ablation electrodes include two ring electrodes disposed proximate to the distal end of the catheter 105.

In certain designs, the pair of ablation electrodes are spaced apart in a selected distance, for example, to form relatively uniformed electrical fields while reducing arcing. In some embodiments, the selected distance is about 1-2 millimeters. In certain embodiments, the selected distance is about 1.4-1.8 millimeters. In some examples, the selected distance is greater than a predetermined lower threshold distance (e.g., 0.5 millimeters), for example, to reduce arcing. In certain examples, the selected distance is smaller than a predetermined upper threshold distance (e.g., 3 millimeters), for example, to generate generally uniformed electric fields. If the distance between the pair of ablation electrodes is substantially greater than the predetermined upper threshold distance, the electrical field generated by the ablation electrodes may not be homogeneous.

In embodiments, the electrode positions and sizes are specifically designed to allow flexibility. For example, the electrodes are designed to be relatively short in length. As another example, two electrodes have a relatively larger spacing to allow flexibility and/or deflection. In some examples, the one or more electrodes include one or more pairs of ablation electrodes and one or more pairs of sensing electrodes. The sensing electrodes may be used to sense electrical signals related to a patient's heart, which allows an operator or a system to determine whether ablation has occurred or not. In some designs, the electrical signals can be used to determine a location or proximate location of the electroporation catheter 105.

In some embodiments, the one or more sensing electrodes on the electroporation catheter 105 can measure electrical signals and generate output signals that can be processed by a controller (e.g., the controller 90) to generate an electro-anatomical map. In some instances, electro-anatomical maps are generated before ablation for determining the electrical activity of the cardiac tissue within a chamber of interest. In some instances, electro-anatomical maps are generated after ablation in verifying the desired change in electrical activity of the ablated tissue and the chamber as a whole. The sensing electrodes may be used to determine the position of the catheter 105 in three-dimensional space within the body. For example, when the operator moves the catheter 105 within a cardiac chamber of a patient, the boundaries of catheter movement can be determined by the controller 90, which may include or couple to a mapping and navigation system, to form the anatomy of the chamber. The chamber anatomy may be used to facilitate navigation of the catheter 105 without the use of ionizing radiation such as with fluoroscopy, and for tagging locations of ablations as they are completed in order to guide spacing of ablations and aid the operator in fully ablating the anatomy of interest.

In some embodiments, other sensors, such as force sensors, degree-of-freedom ("DoF") sensors, are disposed between electrodes. In some implementations, the ablation electrode pair includes two electrodes having similar electrode surface areas. For example, an electrode surface area of a cap electrode includes the surface area at the end surface. In some embodiments, the two ablation electrodes of the ablation electrode pair has a surface area difference within 50% of one of the electrode surface area. In certain embodiments, the two ablation electrodes of the ablation electrode pair has a surface area difference within 30% of one of the electrode surface area. In some embodiments, the two ablation electrodes of the ablation electrode pair has a surface area difference within 20% of one of the electrode surface area. In certain embodiments, the two ablation electrodes of the ablation electrode pair has a surface area difference within 10% of one of the electrode surface area.

In certain embodiments, the one or more electrodes include sensing electrodes smaller than ablation electrodes in size. In one example, each of the sensing electrodes has an electrode surface area no more than 50% of the surface area of an ablation electrode. In another example, each of the sensing electrodes has an electrode surface area no more than 50% of the surface area of each of the ablation electrodes.

According to embodiments, various components (e.g., the controller 90) of the electrophysiological system 50 may be implemented on one or more computing devices. A computing device may include any type of computing device suitable for implementing embodiments of the disclosure. Examples of computing devices include specialized computing devices or general-purpose computing devices such as workstations, servers, laptops, portable devices, desktop, tablet computers, hand-held devices, general-purpose graphics processing units (GPGPUs), and the like, all of which are contemplated within the scope of FIG. 1 with reference to various components of the system 50.

In some embodiments, a computing device includes a bus that, directly and/or indirectly, couples the following devices: a processor, a memory, an input/output (I/O) port, an I/O component, and a power supply. Any number of additional components, different components, and/or combinations of components may also be included in the computing device. The bus represents what may be one or more busses (such as, for example, an address bus, data bus, or combination thereof). Similarly, in some embodiments, the computing device may include a number of processors, a number of memory components, a number of I/O ports, a number of I/O components, and/or a number of power supplies. Additionally, any number of these components, or combinations thereof, may be distributed and/or duplicated across a number of computing devices.

In some embodiments, the system 50 includes one or more memories (not illustrated). The one or more memories includes computer-readable media in the form of volatile and/or nonvolatile memory, transitory and/or non-transitory storage media and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In some embodiments, the one or more memories store computer-executable instructions for causing a processor (e.g., the controller 90) to implement aspects of embodiments of system components discussed herein and/or to perform aspects of embodiments of methods and procedures discussed herein.

Computer-executable instructions may include, for example, computer code, machine-useable instructions, and the like such as, for example, program components capable of being executed by one or more processors associated with a computing device. Program components may be programmed using any number of different programming environments, including various languages, development kits, frameworks, and/or the like. Some or all of the functionality contemplated herein may also, or alternatively, be implemented in hardware and/or firmware.

In some embodiments, the memory may include a data repository may be implemented using any one of the configurations described below. A data repository may include random access memories, flat files, XML files, and/or one or more database management systems (DBMS) executing on one or more database servers or a data center. A database management system may be a relational (RDBMS), hierarchical (HDBMS), multidimensional (MDBMS), object oriented (ODBMS or OODBMS) or object relational (ORDBMS) database management system, and the like. The data repository may be, for example, a single relational database. In some cases, the data repository may include a plurality of databases that can exchange and aggregate data by data integration process or software application. In an exemplary embodiment, at least part of the data repository may be hosted in a cloud data center. In some cases, a data repository may be hosted on a single computer, a server, a storage device, a cloud server, or the like. In some other cases, a data repository may be hosted on a series of networked computers, servers, or devices. In some cases, a data repository may be hosted on tiers of data storage devices including local, regional, and central.

Various components of the system 50 can communicate via or be coupled to via a communication interface, for example, a wired or wireless interface. The communication interface includes, but not limited to, any wired or wireless short-range and long-range communication interfaces. The wired interface can use cables, umbilicals, and the like. The short-range communication interfaces may be, for example, local area network (LAN), interfaces conforming known communications standard, such as Bluetooth® standard, IEEE 802 standards (e.g., IEEE 802.11), a ZigBee® or similar specification, such as those based on the IEEE 802.15.4 standard, or other public or proprietary wireless protocol. The long-range communication interfaces may be, for example, wide area network (WAN), cellular network interfaces, satellite communication interfaces, etc. The communication interface may be either within a private computer network, such as intranet, or on a public computer network, such as the internet.

Figure 2A:
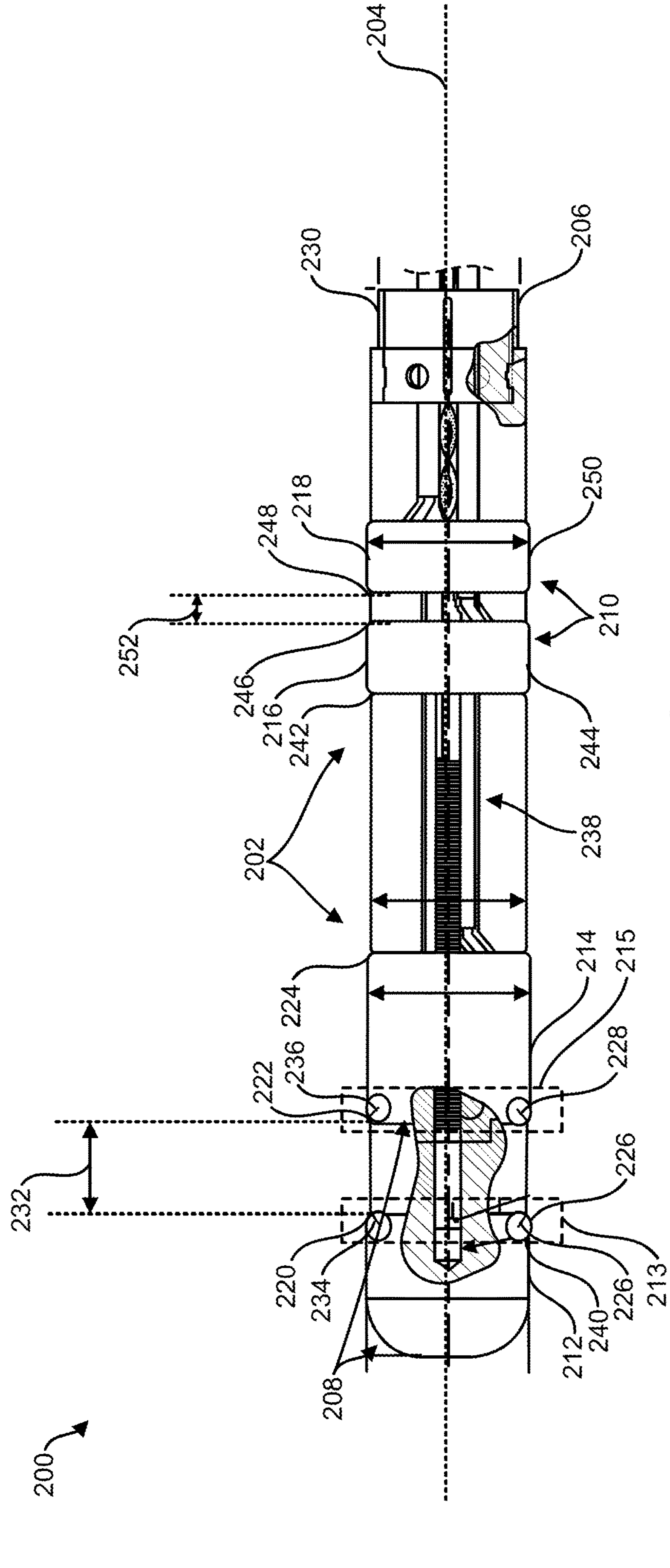
FIG. 2A is an exposed side view of a schematic illustration of an example point electroporation ablation catheter, in accordance with embodiments of the subject matter of the disclosure.
Figure 2B:
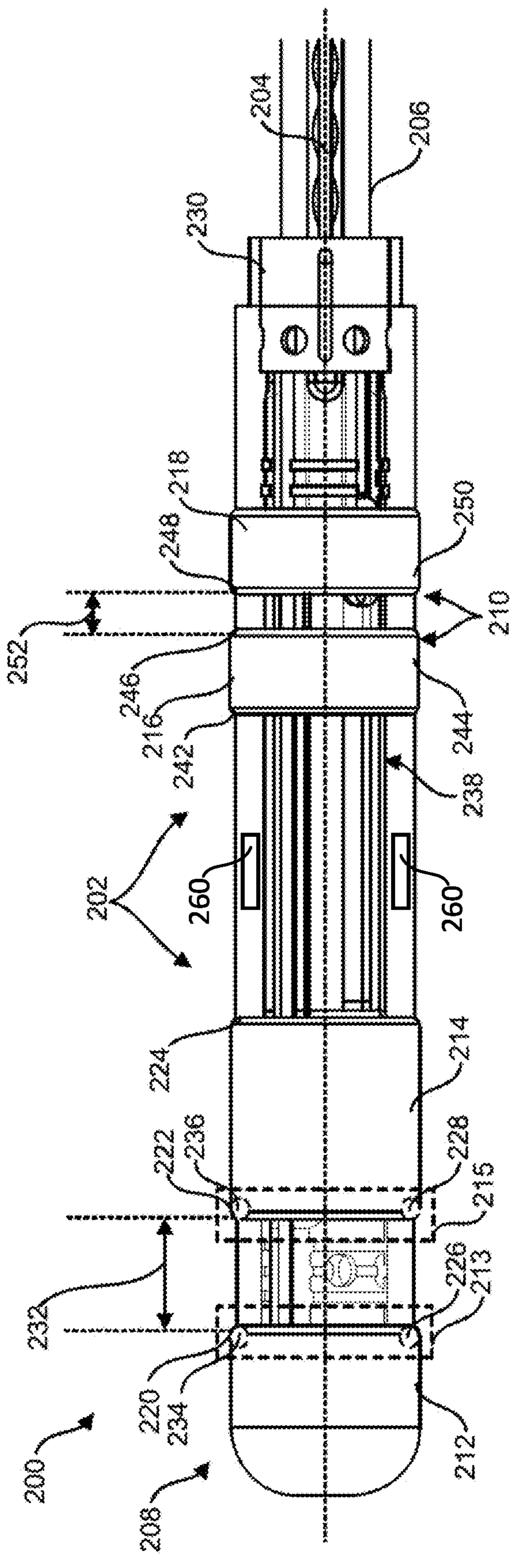
FIG. 2B is a side view of a schematic illustration of an example point electroporation ablation catheter, in accordance with embodiments of the subject matter of the disclosure.
Figure 2C:
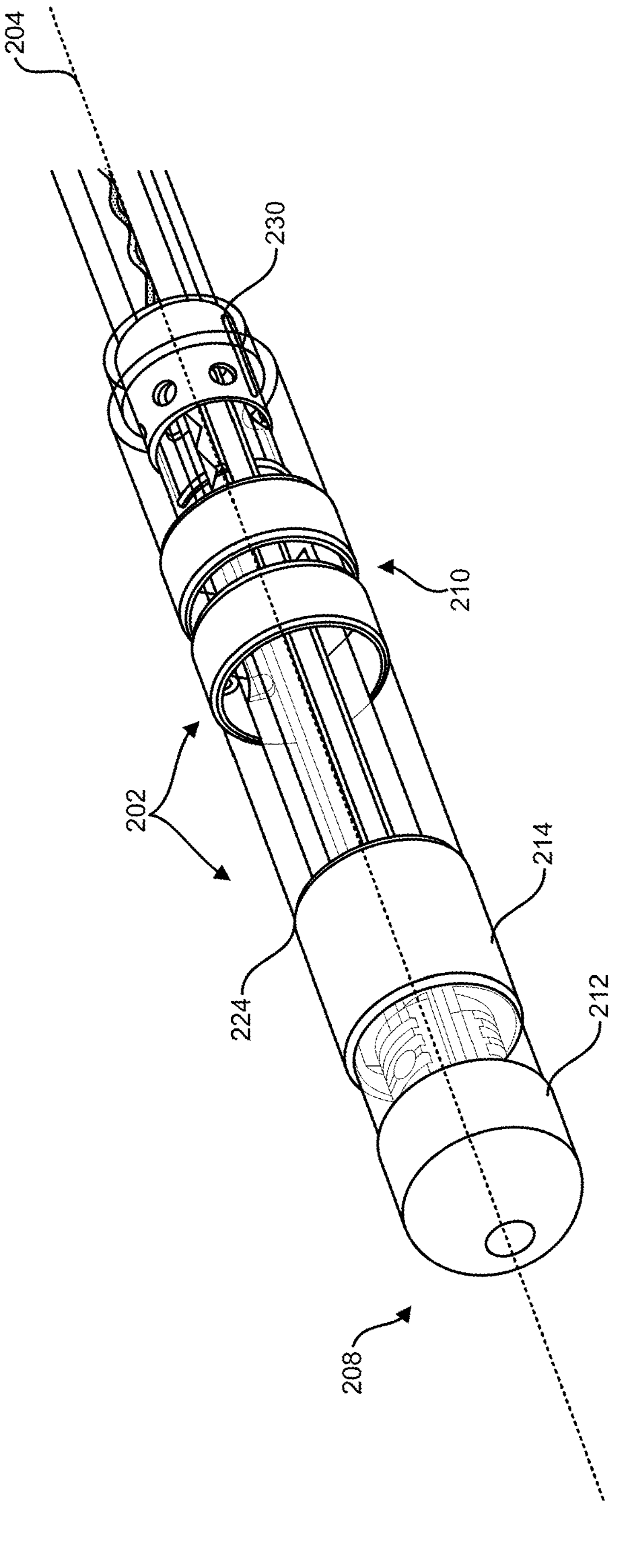
FIG. 2C is a perspective view of a schematic illustration of an example point electroporation ablation catheter, in accordance with embodiments of the subject matter of the disclosure.

FIGS. 2A-2C are exposed side view, side view, and perspective view of a schematic illustration of an example point electroporation ablation catheter 200, in accordance with embodiments of the subject matter of the disclosure.

As shown, the electrode assembly 202 are disposed axially along a longitudinal axis 204 of the shaft 206 of the ablation catheter 200. The electrode assembly 202 includes a first pair of electrodes 208 and a second pair of electrodes 210. The first pair of electrodes 208 may include a first electrode 212 and a second electrode 214 disposed proximate to the distal end of the shaft 206. The second pair of electrodes 210 may include a third electrode 216 and a fourth electrode 218. The first electrode 212 has first edge 220 generally perpendicular to the longitudinal axis 204. The second electrode 214 has a second edge 222 and a third edge 224, both generally perpendicular to the longitudinal axis 204. In embodiments, the first and second edge 220, 222 are generally parallel to each other, and perpendicular to the longitudinal axis 204 such that the electrodes 212, 214 are aligned co-axially with each other. Electrodes disposed out of alignment may increase chances of arc formation.

In embodiments, the first edge 220 of the first electrode 212 is closer to the second edge 222 of the second electrode 214 than the third edge 224 of the second electrode 214. In embodiments, the first electrode 212 has a first edge portion 213 including the first edge 220 and a first edge radius 234, the first edge 220 being generally perpendicular to the longitudinal axis 204. In embodiments, the first electrode 212 has a first cross-sectional shape (not shown) of the first edge portion 213, the cross-sectional shape being generally along the longitudinal axis 204 and rounded at a first corner 226.

In embodiments, the second electrode 214 has a second edge portion 215 including the second edge 222 and a second edge radius 236. In embodiments, the second edge 222 has a second cross-sectional shape (not shown) of the second edge portion 215, and the second cross-sectional shape being generally along the longitudinal axis 204 and rounded at a second corner 228. The first and second edge radius 234, 236 varies depending on the material thickness used for the first and second electrodes 212, 214. The rounded shape at the corners 226, 228 can decrease chances of arc formation during treatment.

In some embodiments, the first electrode 212 includes a conductive material having a first thickness, and the first edge radius is associated with the first thickness. In some instances, the first thickness may be around 0.0762-0.1524 millimeters (or 0.003-0.006 inches). In some embodiments, the second electrode 214 includes a conductive material having a second thickness, and the second edge radius is associated with the second thickness. In some instances, the second thickness may be around 0.0762-0.1524 millimeters (or 0.003-0.006 inches).

The first electrode 212 has a first electrode surface area, and the second electrode 214 has a second electrode surface area. In embodiments, the difference between the first electrode surface area and the second electrode surface area is less than 50% of the first electrode surface area. In certain embodiments, the difference between the first electrode surface area and the second electrode surface area is less than 20% of the first electrode surface area. In some embodiments, the difference between the first electrode surface area and the second electrode surface area is less than 10% of the first electrode surface area. The difference between the first electrode surface area and the second electrode surface area can be useful in reducing arcing, as the larger the difference between the two surface areas, the more likely that arc or spark would form during treatment. In other words, an equal surface area between the two electrodes would prevent arc formation. However, since energy tends toward a smaller surface area, a small offset or difference between the surface areas is needed to steer current necessary for the treatment.

In some embodiments, the distance 232 between the first edge 220 and the second edge 222 is in the range of 1-2 millimeters. In some embodiments, the distance between the first edge 220 and the second edge 222 is in the range of 1.4-1.8 millimeters. In some embodiments, the distance between the first edge 220 and the second edge 222 is around 1.6 millimeters. If the distance 232 is too small, the risk of arc or spark formation would increase. If the distance 232 is too large, the risk of non-homogeneous lesion formation would increase. In other words, if the distance 232 is too large, the electric field created by the electrodes 212, 214 may be non-homogeneous, which affects the IRE treatment negatively.

In some embodiments, the second pair of electrodes 210 may be sensing electrodes configured to measure an electrical signal. In other embodiments, the second pair of electrodes 210 may also be ablation electrodes connected to an electroporation generator. In some instances, the second pair of electrodes 210 are configured to measure local impedance, and may act as magnetic sensors for mapping local electric fields in 5 degrees of freedom (e.g., 5 different motions—x, y, z, acceleration, and rotation).

The distance between the third edge 224 and a fourth edge 242 of a distal electrode 244 of the second pair of electrodes 210 may be around 4.5 millimeters to include a force sensor disposed in between electrodes 214, 244. In embodiments, the catheter may include a force sensor 260, as shown in FIG. 2B, disposed in between electrodes 214, 244, and configured to sense force of local electric fields. In embodiments, the catheter does not include a force sensor, and the gap between the third edge 224 and a fourth edge 242 of a distal electrode 244 of the second pair of electrodes 210 may be smaller than 4.5 millimeters. The force sensor 260 is configured to measure a force when a tip of the catheter 200 is in contact with tissue of a patient, which may provide an operator or a system with feedback on whether the catheter tip is in close proximity to the tissue being treated. The addition of a force sensor and force information at the catheter tip may also help the operator to avoid perforation of the cardiac tissue, and therefore can be helpful for safety purposes.

The distance 252 between the fifth edge 246 of the third electrode 216 and the sixth edge 248 of the fourth electrode 250 may be between 0.5 mm-4.5 mm. In some embodiments, the distance 252 may be between 1-2 mm. In some embodiments, the distance 252 may be 1.6 mm. In some embodiments, the distance 252 may be within 10% of the diameter of the electrodes 216, 218, which are 2.79 mm.

In some embodiments, the first and second pair of electrodes may have a surface finish having a roughness up to 0.0008 millimeters (or 30 micro inches) RA ("Arithmetic mean roughness"). In some instances, the conductive materials may include 90% of Platinum and 10% of Aradium™.

The electrode assembly 202 is connected to an electroporation generator (e.g., electroporation generator 130 in FIG.

1) via one or more conductor wires 238. Where the wires 238 are connected to the electrodes 212, 214 is not of crucial importance to the present invention. In embodiments, the conductor wires are made of metal, and the exposed point of the metal is covered between electrodes 212, 214 to prevent arc formation. In some embodiments, the conductor wires are made of copper with nickel plating or coating to provide good conductive quality. Copper may be prone to corrosion, but the corrosion may create an oxidized layer for better conductive quality. In some instances, the conductor wires may include steel. In some instances, the conductor wires may include solid nickel.

The ablation catheter 200 is constructed to withstand generator output energy from the electroporation generator up to 3000 volts of direct current (VDC). In some instances, in order to prevent current leakage, dielectric materials are used to isolate the electrodes 212, 214, 216, and 218 (e.g., injection molding multiple polymer and adhesive layers for insulation). Each conductor wire may be insulated from another conductor or electrode with polymer insulation (e.g., polyimide, polyether ether ketone (PEEK), thermoplastic elastomers, polycarbonate, or polynylon). In some embodiments, the insulation layers are provided with redundancy to ensure a dielectric strength in the event that one of the insulators is compromised.

In some embodiments, the electrode assembly 202 includes a fifth ring electrode 230 disposed further away from the distal end of the shaft 206 of the ablation catheter 200 than each electrode of the first pair of electrodes 208. The distance between the third edge 224 of the first pair of electrodes 208 and the ring electrode 230 may be around 4.5 mm. In some embodiments, a steering ring may be disposed proximal to the fifth electrode 230 along the longitudinal axis 204. The steering ring (e.g., the fifth electrode 230) is configured to help deflect the distal tip of the catheter 200.

In some embodiments, there may be more than five electrodes (e.g., six, seven, or a higher number). In some instances, the additional electrodes may be configured to add additional ablation vectors/configurations (e.g. different cathode/anode pairing or selection options) in order to change the shape of the electric field being created. In some instances, the additional electrodes may be configured for different sensing capabilities, including sensing cardiac electrical activity and/or for use in mapping cardiac electrical activity or anatomy.

In some embodiments, the catheter 200 may include a navigation sensor 240 disposed at the distal end of the shaft 206, internal to the first electrode 212. The navigation sensor 240 is configured to sense movement and position of the distal end of the catheter 200 in 5 degrees of freedom/motions.

Figure 3:
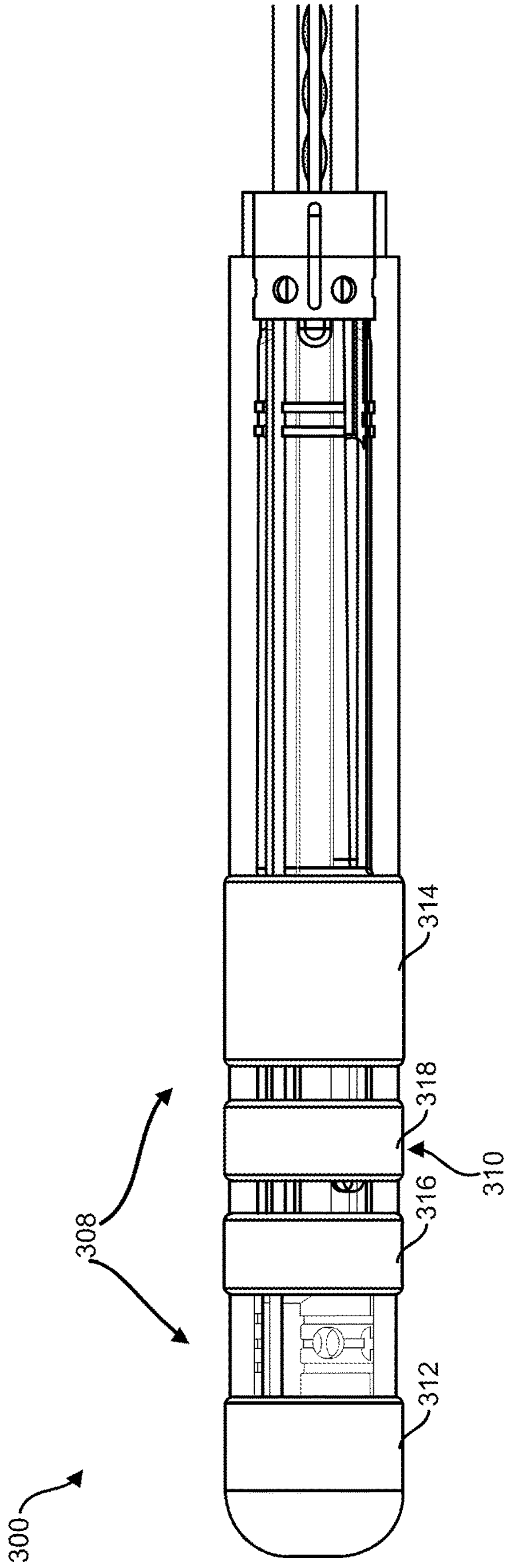
FIG. 3 is a side view of a schematic illustration of an example point electroporation ablation catheter, in accordance with embodiments of the subject matter of the disclosure.

FIG. 3 is a side view of a schematic illustration of an example point electroporation ablation catheter 300, in accordance with embodiments of the subject matter of the disclosure. The ablation catheter 300 may include a first pair of electrodes 308 and a second pair of electrodes 310. The first pair of electrodes 308 may include a first electrode 312 and a second electrode 314. The second pair of electrodes 310 may include a third electrode 316 and a fourth electrode 318. In some embodiments, as shown, the second pair of electrodes 310 may be disposed between the first electrode 312 and the second electrode 314. In some embodiments, the first pair of electrodes 308 may be ablation electrodes whereas the second pair of electrodes may be sensing electrodes. In some embodiments, both the first pair and the second pair of electrodes 308, 310 may be ablation electrodes, and one or more additional electrodes may be added for purposes mentioned above (e.g., to add additional ablation vectors/configurations, or for different sensing capabilities, including sensing cardiac electrical activity and/or for use in mapping cardiac electrical activity or anatomy).

Figure 4:
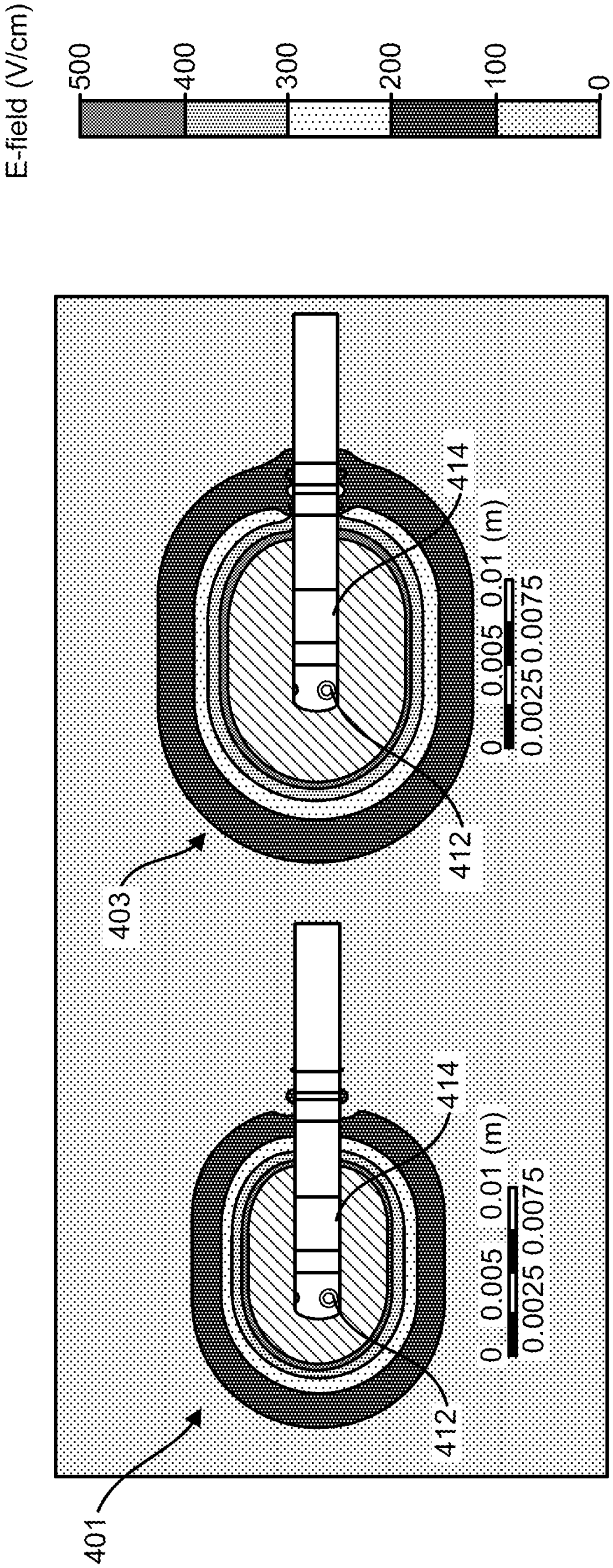
FIG. 4 shows an exemplary electric field of a point electroporation ablation catheter, in accordance with embodiments of the subject matter of the disclosure, in accordance with embodiments of the subject matter of the disclosure.

FIG. 4 shows an example electric field of a point electroporation ablation catheter, in accordance with embodiments of the subject matter of the disclosure. Electric field 401 is generated by the first pair of electrodes 412, 414 under 1000 volts. Electric field 403 is generated by the first pair of electrodes 412, 414 under 2000 volts. As shown, the field 403 is larger in size compared to the field 414 due to the higher voltage. The shape of both fields 401, 403 is relatively homogeneous, for example, the field strength is generally equivalent relative to the distance to either electrode (e.g., generally same field strength for areas with generally same distances from electrodes), such that arcing is reduced. As illustrated, the electrical field has no obvious gap between the two electric fields generated by electrodes 412, 414 or significant differences in field strength relative to distances to electrodes.

Figure 5:
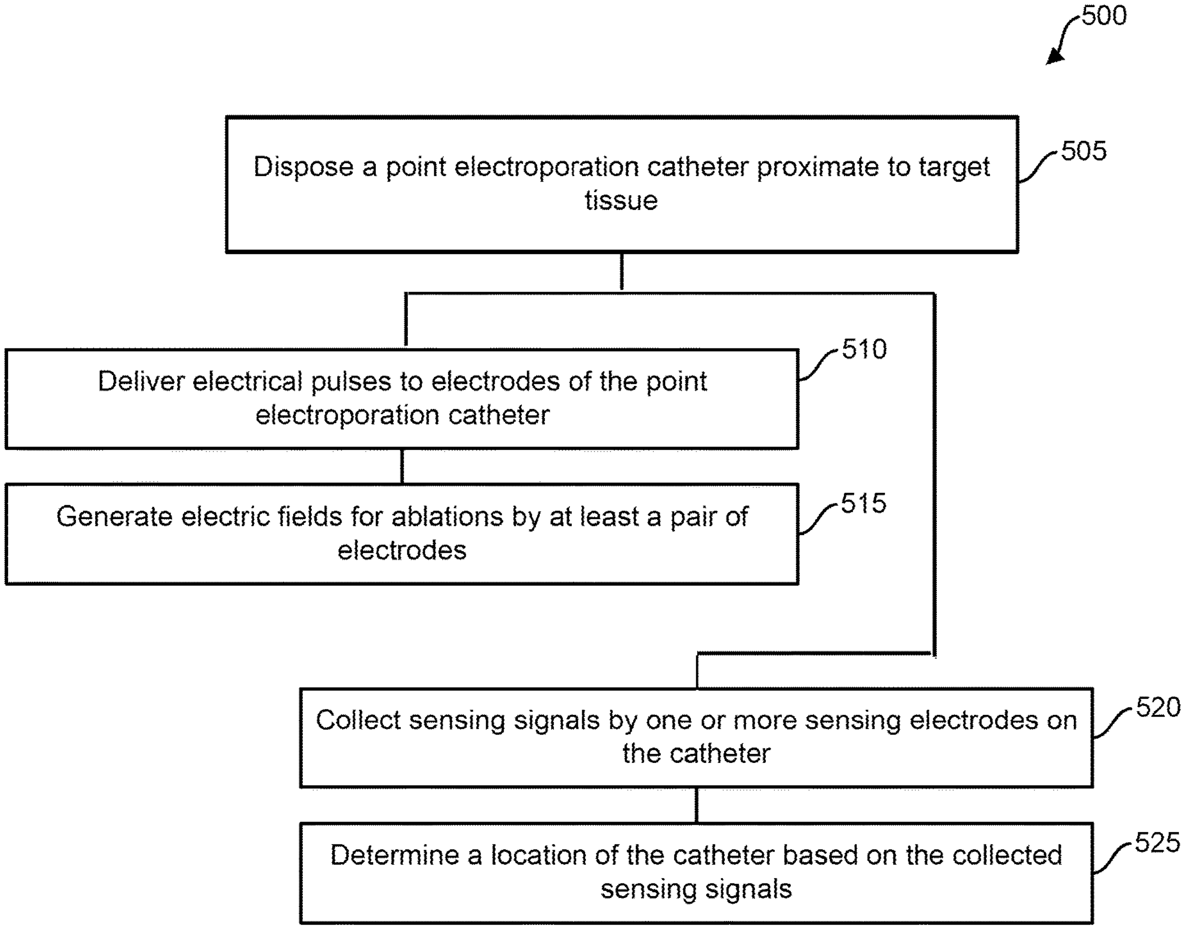
FIG. 5 is a flow diagram illustrating a method of treating target tissue by electroporation ablation, in accordance with embodiments of the subject matter of the disclosure.

FIG. 5 is a flow diagram illustrating a method 500 of treating target tissue with an electroporation catheter, in accordance with embodiments of the subject matter of the disclosure. Aspects of embodiments of the method 500 may be performed, for example, by an electroporation ablation system/device (e.g., the system/device 50 depicted in FIG. 1). One or more steps of method 500 are optional and/or can be modified by one or more steps of other embodiments described herein. Additionally, one or more steps of other embodiments described herein may be added to the method 500.

In some embodiments, the method 500 includes disposing a point electroporation catheter proximate to a target tissue (505) and delivering electrical pulses to electrodes of the point electroporation catheter (510). In some examples, the point electroporation catheter including a shaft defining a longitudinal axis and a first pair of electrodes, where the first pair of electrodes includes a first electrode disposed proximate to a distal end of the shaft and a second electrode disposed proximate to the first electrode. In certain examples, the first electrode has a first electrode surface area, the second electrode has a second electrode surface area. In one example, a difference between the first electrode surface area and the second electrode surface area being less than 50% of the first electrode area. In one example, a difference between the first electrode surface area and the second electrode surface area being less than 20% of the first electrode area. In one example, a difference between the first electrode surface area and the second electrode surface area being less than 10% of the first electrode area.

The method 500 may further include generating electric fields for ablations by at least a pair of electrodes (515), for example, by the first pair of electrodes. In embodiments, the electric field is generated by the first pair of electrodes proximate to the target tissue in response to a plurality of electrical pulse sequences delivered in a plurality of therapy sections, the electric field having electric field strength sufficient to ablate the target tissue via irreversible electroporation.

In embodiments, the first electrode has a first edge portion generally perpendicular to the longitudinal axis, and the second electrode comprises a second edge portion generally perpendicular to the longitudinal axis and a third edge portion generally perpendicular to the longitudinal axis. In some instances, the first edge portion is closer to the second edge portion than the third edge portion. In some embodiments, a first cross-sectional shape of the first edge portion along the longitudinal axis is rounded at a first corner with a first edge radius, and a second cross-sectional shape of the second edge portion is rounded at a second corner with a second edge radius.

In embodiments, the point electroporation catheter further comprises a second pair of electrodes disposed adjacent to the first pair of electrodes and comprising a third electrode and a fourth electrode. In some examples, the second pair of electrodes are sensing electrodes. In certain examples, the second pair of electrodes are ablation electrodes. The method 500 may include collecting sensing signals by the sensing electrodes on the catheter (520), for example, using the second pair of electrodes. In some embodiments, the method 500 includes determining a location of the catheter based on the collected sensing signals (525). For example, the sensing electrodes may be a part of a location tracking system. In one example, the sensing electrodes can measure local impedances, which can be used to determine the location of the catheter. In some embodiments, the method includes generating an electro-anatomical map based on the collected sensing signals. The sensing electrodes may collect sensing signals before and/or after the ablation.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An electroporation ablation system for treating target tissue in a patient, the electroporation ablation system comprising:

an electroporation ablation device comprising:

a shaft having an elongated body defining a longitudinal axis, the elongated body having a distal end and a proximal end;

a force sensor configured to sense a force of local electric fields;

an electrode assembly disposed on the shaft comprising:

a first pair of electrodes comprising a first electrode disposed proximate to the distal end of the elongated body and a second electrode; and a second pair of electrodes disposed adjacent to the first pair of electrodes and comprising a third electrode and a fourth electrode;

a controller configured to receive one or more signals from the one or more mapping electrodes; and an electroporation generator operatively coupled to the electrode assembly and the controller;

wherein the first electrode comprises a first edge portion generally perpendicular to the longitudinal axis;

wherein the second electrode comprises a second edge portion generally perpendicular to the longitudinal axis and a third edge portion generally perpendicular to the longitudinal axis;

wherein the first edge portion is closer to the second edge portion than the third edge portion;

wherein a first side view of the first edge portion along the longitudinal axis is rounded at a first corner with a first edge radius;

wherein a side view of the second edge portion is rounded at a second corner with a second edge radius; and wherein the force sensor is disposed between the second electrode and the second pair of electrodes.

2. The electroporation ablation system of claim 1, wherein the force sensor is configured to measure a force when the distal end is in contact with tissue of a patient.

3. The electroporation ablation system of claim 1, further comprising a fifth electrode.

4. The electroporation ablation system of claim 3, wherein the fifth electrode is configured as a steering ring.

5. The electroporation ablation system of claim 1, wherein the second pair of electrodes are sensing electrodes configured to measure an electrical signal.

6. The electroporation ablation system of claim 5, wherein the second pair of electrodes are disposed between the first electrode and the second electrode.

7. The electroporation ablation system of claim 5, wherein the sensing electrodes are configured to measure local impedance and act as magnetic sensors for mapping local electric fields in five degrees of freedom.

8. The electroporation ablation system of claim 7, wherein the controller is configured to generate an electro-anatomical map based on signals received from the sensing electrodes.

9. The electroporation ablation system of claim 1, further comprising a navigation sensor disposed at the distal end of the elongated body and internal to the first electrode, the navigation sensor configured to sense movement and position of the distal end in five degrees of freedom.

10. The electroporation ablation system of claim 1, wherein the first edge portion and the second edge portion are generally parallel to each other such that the first electrode and the second electrode are aligned co-axially with each other along the longitudinal axis.

11. An electroporation ablation device comprising:

a shaft having an elongated body defining a longitudinal axis, the elongated body having a distal end and a proximal end;

a force sensor;

an electrode assembly disposed on the shaft comprising:

a first pair of electrodes comprising a first electrode disposed proximate to the distal end of the elongated body and a second electrode;

a second pair of electrodes disposed adjacent to the first pair of electrodes and comprising a third electrode and a fourth electrode; and a fifth electrode configured as a steering ring;

wherein the first electrode comprises a first edge portion generally perpendicular to the longitudinal axis;

wherein the second electrode comprises a second edge portion generally perpendicular to the longitudinal axis and a third edge portion generally perpendicular to the longitudinal axis;

wherein the first edge portion is closer to the second edge portion than the third edge portion;

wherein a first side view of the first edge portion along the longitudinal axis is rounded at a first corner with a first edge radius;

wherein a second side view of the second edge portion is rounded at a second corner with a second edge radius; and wherein the force sensor is disposed between the second electrode and the second pair of electrodes.

12. The electroporation ablation device of claim 11, wherein the force sensor is configured to sense a force of local electric fields.

13. The electroporation ablation device of claim 11, wherein the force sensor is configured to measure a force when the distal end is in contact with tissue of a patient.

14. The electroporation ablation device of claim 11, wherein the second pair of electrodes are sensing electrodes configured to measure an electrical signal.

15. The electroporation ablation device of claim 14, wherein the second pair of electrodes are disposed between the first electrode and the second electrode.

16. The electroporation ablation device of claim 11, further comprising a navigation sensor disposed at the distal end of the elongated body and internal to the first electrode, the navigation sensor configured to sense movement and position of the distal end in five degrees of freedom.

17. The electroporation ablation device of claim 11, wherein the first edge portion and the second edge portion are generally parallel to each other such that the first electrode and the second electrode are aligned co-axially with each other along the longitudinal axis.

18. The electroporation ablation device of claim 11, further comprising one or more conductor wires electrically connecting the electrode assembly, wherein the one or more conductor wires are covered between the first electrode and the second electrode to prevent arc formation.

19. An electroporation ablation system for treating target tissue in a patient, the electroporation ablation system comprising:

an electroporation ablation device comprising:

a shaft having an elongated body defining a longitudinal axis, the elongated body having a distal end and a proximal end;

a force sensor configured to sense a force of local electric fields;

an electrode assembly disposed on the shaft comprising:

a first pair of electrodes comprising a first electrode disposed proximate to the distal end of the elongated body and a second electrode;

a second pair of electrodes disposed adjacent to the first pair of electrodes and comprising a third electrode and a fourth electrode; and a fifth electrode configured as a steering ring;

a controller configured to receive one or more signals from the one or more mapping electrodes; and an electroporation generator operatively coupled to the electrode assembly and the controller;

wherein the first electrode comprises a first edge portion generally perpendicular to the longitudinal axis;

wherein the second electrode comprises a second edge portion generally perpendicular to the longitudinal axis and a third edge portion generally perpendicular to the longitudinal axis;

wherein the first edge portion is closer to the second edge portion than the third edge portion;

wherein a first side view of the first edge portion along the longitudinal axis is rounded at a first corner with a first edge radius;

wherein a side view of the second edge portion is rounded at a second corner with a second edge radius; and wherein the force sensor is disposed between the second electrode and the second pair of electrodes.

20. The electroporation ablation system of claim 19, wherein the force sensor is configured to measure a force when the distal end is in contact with tissue of a patient.

* * * * *